United States Patent [19]

Dearman et al.

[11] Patent Number: 5,651,361
[45] Date of Patent: Jul. 29, 1997

[54] BREATHING APPARATUS

[75] Inventors: Peter Thomas Dearman, Bishop's Stortford; Howard Alfred Buckenham, Chelmsford, both of United Kingdom; Kevin Bowden, Orangeville, Canada; Andrew Sharpe, Saffron Walden; Damon Andrew Cookman, Bishop's Stortford, both of United Kingdom

[73] Assignee: BNOS Electronics Limited, Great Dunmow, United Kingdom

[21] Appl. No.: 542,361

[22] Filed: Oct. 12, 1995

Related U.S. Application Data

[63] Continuation of Ser. No. 129,105, filed as PCT/GB92/00584, Apr. 2, 1992, Pat. No. 5,537,999.

[30] Foreign Application Priority Data

Apr. 3, 1991 [GB] United Kingdom .................. 9106960

[51] Int. Cl.$^6$ ................................................. A61M 39/22
[52] U.S. Cl. .................. 128/205.25; 128/204.18; 128/205.13; 128/205.14; 128/205.24
[58] Field of Search .................. 128/204.18, 205.13, 128/205.14, 205.24, 205.25, 206.26, 204.26, 203.29, 203.15

[56] References Cited

U.S. PATENT DOCUMENTS

| | | | |
|---|---|---|---|
| 1,848,234 | 8/1932 | Swope et al. | 128/205.24 |
| 2,920,623 | 8/1960 | Holt | 128/205.24 |
| 3,874,378 | 4/1975 | Isaacson et al. | 128/205.24 |
| 4,832,016 | 5/1989 | Berg | 128/205.24 |
| 4,898,174 | 2/1990 | Fangrow, Jr. | 128/204.26 |
| 5,067,487 | 11/1991 | Bauman | 128/205.13 |

FOREIGN PATENT DOCUMENTS

| | | |
|---|---|---|
| 217004 | 4/1986 | United Kingdom . |
| 9001965 | 3/1990 | WIPO . |

*Primary Examiner*—Vincent Millin
*Assistant Examiner*—William J. Deane, Jr.
*Attorney, Agent, or Firm*—Lee, Mann, Smith, McWilliams, Sweeney & Ohlson

[57] ABSTRACT

Breathing apparatus supplies air or oxygen to a patient and comprises a hand-held housing (10), a gas inlet on the housing, a gas outlet (12) on the housing (10), and a manual/automatic switch (16) on the housing for supplying gas either to a manually operable valve (40) or to a main valve (48) which delivers gas to the outlet on a cyclic basis. A trigger (22) on the housing (10) controls the supply of gas to the outlet through the manually operable valve (40).

3 Claims, 4 Drawing Sheets

BREATHING APPARATUS

RELATED APPLICATIONS

This application is a continuation of U.S. patent application Ser. No. 08/129,105, filed Sep. 30, 1993, now U.S. Pat. No. 5,537,999, which is the national filing of International application No. PCT/GB92/00584 filed Apr. 2, 1992.

FIELD OF THE INVENTION

This invention relates to breathing apparatus for supplying breathable gas to a patient. Such apparatus can be used for emergency resuscitation and also as a lung ventilator for persons under anaesthesia.

BACKGROUND TO THE INVENTION

Breathing apparatus of the above-described type is known, for example, from U.K. Patent Specification No. 2170409A. This known apparatus includes a gas circuit means incorporating various valves and throttles whereby pulses of air or oxygen can be supplied to the patient on a cyclic basis. It also includes a switch whereby, instead, gas can be supplied to the patient on a continuous basis, the gas circuit means being by-passed.

In known breathing apparatus of the type in question, the gas control circuitry is usually embodied as a control module and a hand piece connected to the control module by a length of flexible tubing. All adjustments are effected at the control module, requiring the user to free at least one hand from the hand piece, which during use has connected to it a face mask which has to be hand held to seal around the patient's mouth and nose.

It is an object of the present invention to provide improved breathing apparatus for supplying breathable gas to a patient.

The invention

According to the invention, there is provided breathing apparatus for supplying air or oxygen to a patient, comprising a housing adapted to be hand held, a gas inlet on the housing, a gas outlet on the housing, gas circuit means within the housing, a switch on the housing whereby gas is either automatically supplied by the circuit means to the gas outlet on a cyclic basis or is supplied continuously to a manually operable valve in the housing, and a manually operable member, preferably a trigger, on the housing for controlling the supply of gas to the outlet through the manually operable valve.

This apparatus has the advantage that, in use, with the face mask attached to the gas outlet on the housing, all adjustments and operations of the apparatus can be carried out with the fingers substantially without relaxing the hands holding the face mask in position. In particular, the trigger can be operated to cause cycling of the gas supply under manual control, for exaample in sympathy with manual cardiac massage.

The hand held instrument in accordance with the invention can be made relatively small and light, for example having dimensions of about 110 mm by 65 mm by 51 mm and weighing about 250 gms, and this is in part made possible by improvements in the gas control circuitry, as compared, for example, with that described in U.K. Patent Specification No. 2170409A.

Preferably the gas flow rate to the patient is controlled by a first adjustable throttle and the periodicity of the cycle is controlled by a second adjustable throttle, the two throttles being combined into a coaxial assembly of inner and outer throttle elements of which the inner throttle element is carried by the outer throttle element.

The throttle elements preferably comprise inner and outer throttle needles adjustable within a fixed sleeve. The outer throttle needle, which is hollow, and preferably controls the gas flow to the patient, is adjustable within the fixed sleeve by means of cooperating screwthreads, whilst the inner throttle needle is in screwthreaded engagement with the outer needle to control the cycle periodicity. Thus, while the cycle periodicity is independently adjustable, adjustment of the gas flow rate to the patient also automatically adjusts cycle timing. This is convenient to enable the provision of an adult/child control on the instrument. Adjustment of the control towards the child setting reduces the gas flow rate to the patient and simultaneously increases the cycle periodicity.

The gas circuit means preferably includes a main valve which produces the gas cycling effect. This main valve has a main gas inlet and a gas outlet from which gas passes to the flow rate/timing throttle means, a secondary gas inlet receiving from the throttle means a proportion of the gas flowing to the patient which is dependent on the setting of the timing needle, and a spring loaded valve member which is gradually driven by build-up of gas pressure at the secondary inlet to a position in which it occludes the main gas inlet, whereupon flow of gas to the throttle means ceases, gas bleeds back from the secondary inlet towards the throttle means, and the valve member is restored eventually to re-open the main inlet. Advantageously, this arrangement of the main valve obviates the need for a gas reservoir, for example as described in U.K. Patent Specification No. 2170409A.

In a preferred instrument, gas enters the inlet to the housing and passes to a manual/auto switch, preferably after passing through an adjustable pressure regulator, the manual/auto switch directing the gas either to the trigger operable manual valve or to the main inlet of the above-described main valve of the gas recycling circuit.

In addition to a pressure relief valve at the gas flow outlet to the patient, the apparatus preferably includes a respiratory assist valve which is operable, if the patient attempts to inhale during a gas-off phase of a cycle, immediately to relieve pressure at the secondary inlet of the main valve thereby at once to initiate a gas-on phase.

DESCRIPTION OF EMBODIMENT

Further features of the invention will be apparent from the following description of a practical embodiment of apparatus, making reference to the accompanying drawings, in which.

Figure 1:
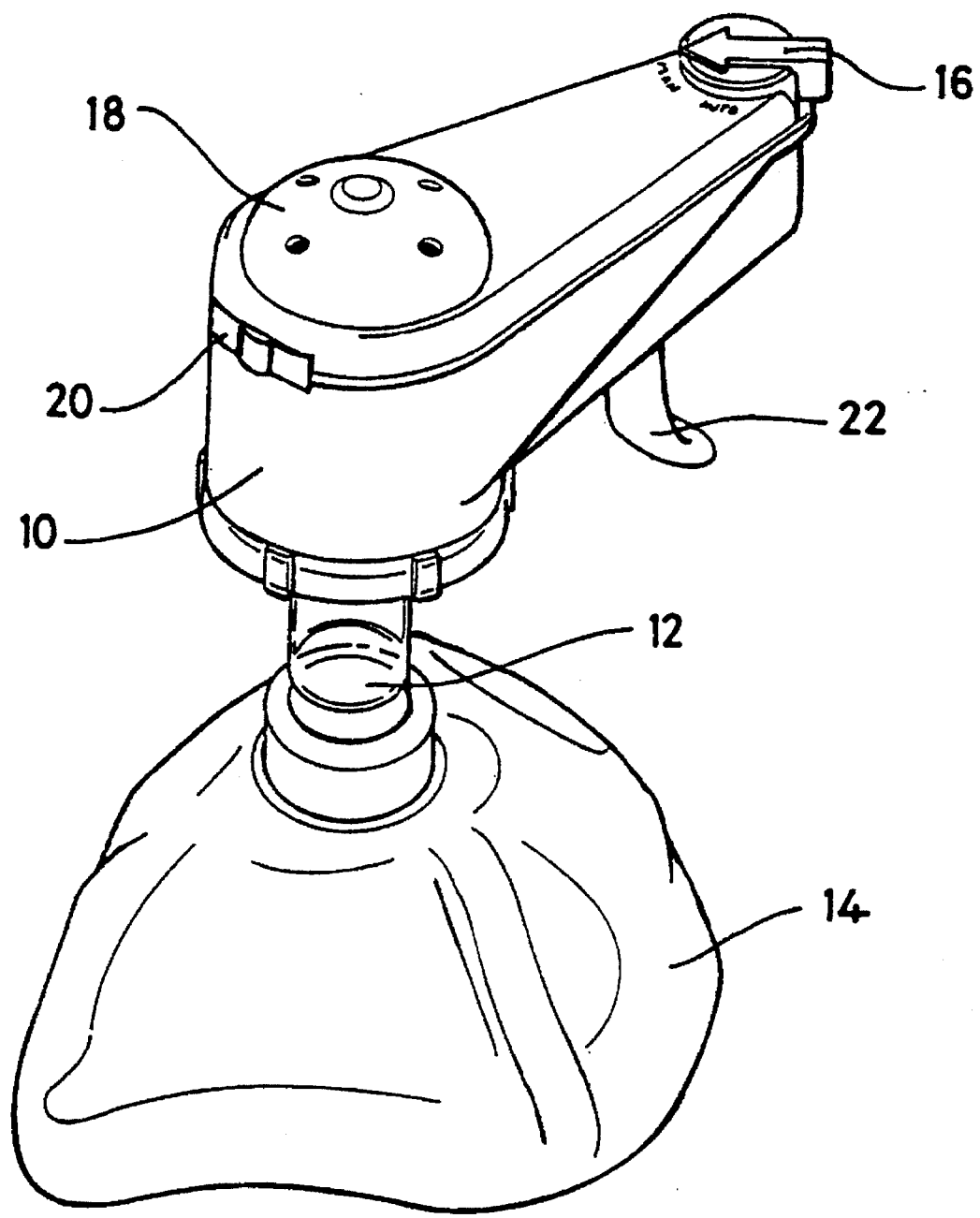
FIG. 1 shows the embodiment in perspective view, with a face mask attached.

Referring first to FIG. 1, the preferred apparatus or instrument comprises a housing 10 convenient for hand holding, and having a gas outlet 12 to which has been attached a face mask 14.

The housing has a manual/auto switch 76, a pressure relief or blow-off valve 18 associated with the gas outlet, a control 20 fully adjustable between adult and child settings, and a manual trigger 22.

The housing also has a gas inlet, not visible in FIG. 1, to which air or oxygen is supplied from a storage cylinder or a pipeline.

As will be described in detail later, within the housing the instrument has gas control circuitry whereby breathable gas can either be supplied as pulses on a cyclic basis, i.e. when the switch 16 is on the auto setting, or be supplied to a manually operable valve controllable by the trigger 22, i.e. when the switch 16 is on the manual setting. When gas is delivered on a cyclic basis, the gas flow rate and cycle timing are adjustable by means of the control 20.

Figure 2:
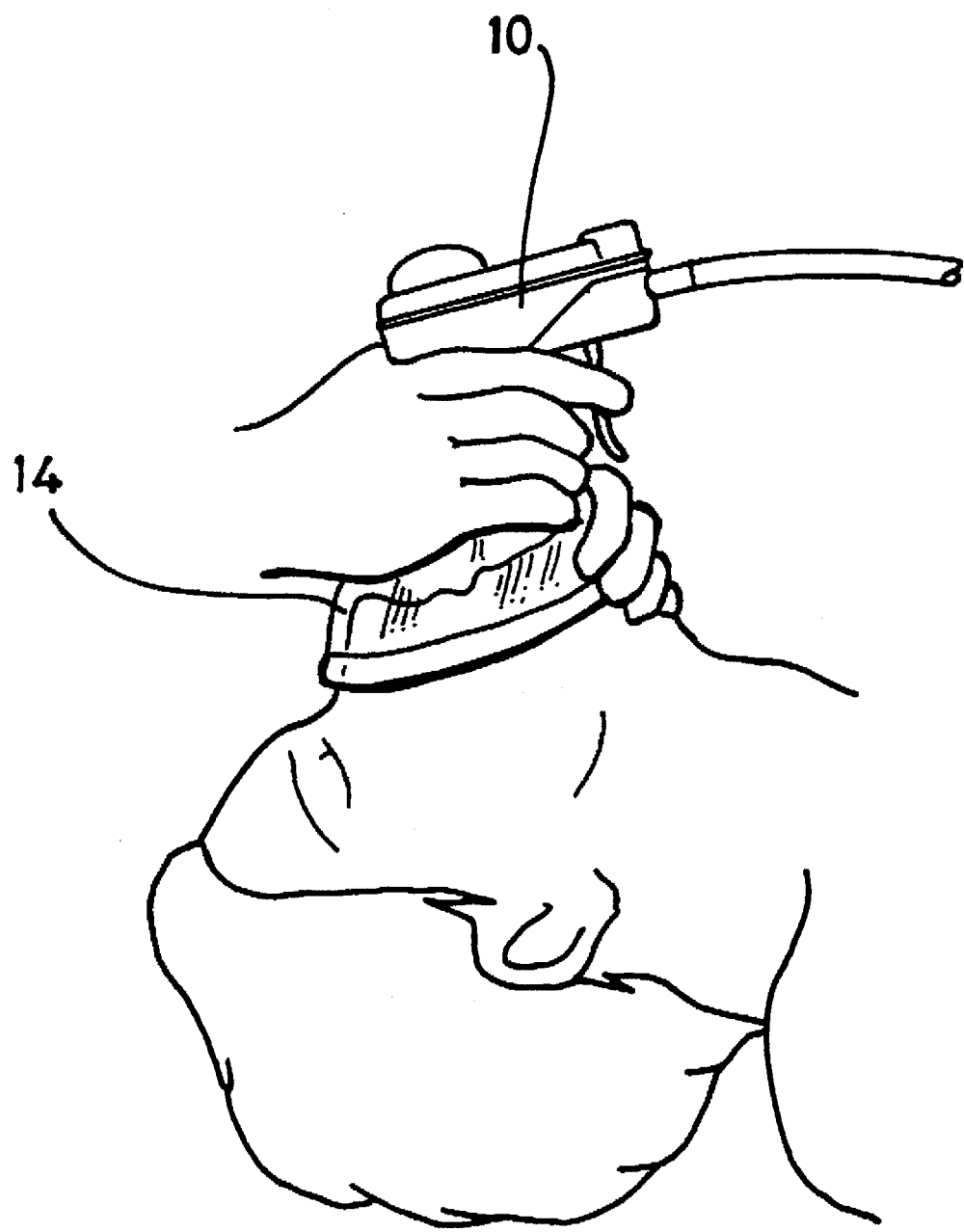
FIG. 2 shows the manner of use of the instrument.

FIG. 2 shows the manner of use of the instrument. While both hands can be used to hold the instrument with attached face mask to ensure a good seal of the mask around the mouth and nose of the patient, at the same time all the instrument controls, and especially the trigger 22, can readily be operated with the fingers without relaxing hold on the instrument and face mask. In the manual mode, for example, the trigger 22 can readily be operated to deliver pulses of gas in sympathy with manual cardiac massage.

Figure 3:
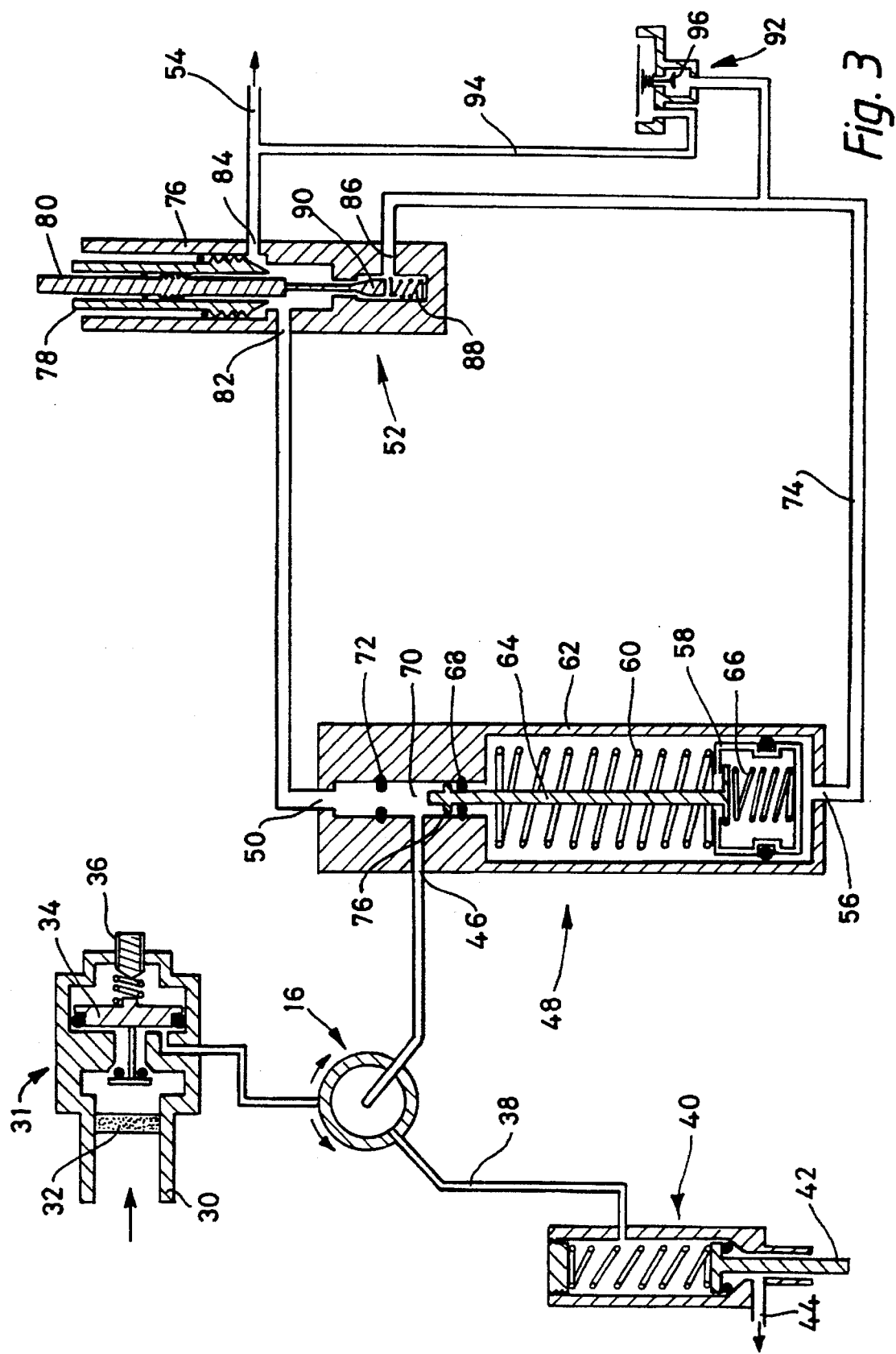
FIG. 3 shows the gas control circuit within the housing of the instrument.

The gas control circuitry within the housing is shown in FIG. 3. Gas enters at an inlet 30 through a sintered bronze filter 32 to a pressure regulator 34 having an adjustment screw 36. The filter 32, regulator 34 and screw 36 are mounted in a regulator housing 31.

From the pressure regulator, the gas passes to the manual/auto switch 16, which in its manual setting passes gas on the line 38 to the manual valve 40 operable by the trigger-connected element 42. When the trigger is depressed, gas is delivered to the patient from outlet 44.

In the auto setting of the switch 16, gas passes to the main inlet 46 of a main valve 48, having an outlet 50 from which gas passes to a throttle unit 52. At the throttle unit, a major proportion of gas passes to the patient outlet 54, which combines with the gas outlet 44 to provide the common gas outlet 12 from the housing shown in FIGS. 1 and 2. A minor proportion of gas is diverted from the throttle unit 52 back to a secondary inlet 56 of the main valve 48.

The main valve 48 has a box piston 58 loaded by a restoring spring 60 and which is a sliding seal fit in the valve casing 62. The piston carries a valve element 64, loaded by a spring 66 to move with said piston, which valve element at its end remote from the piston can slide through an O-ring seal 68 in a passage 70. Normally, therefore, gas enters the main inlet 46 and thence to the outlet 50, as the valve element 64 closes the passage 70 at the seal 68.

However, as gas pressure builds up behind the piston 58 at the secondary inlet 56, the valve element 64 is displaced eventually to close off the main inlet 46 from the outlet 50 at the second O-ring seal 72 in the passage 70. The main inlet 46 thus effectively being occluded, gas flow to the throttle unit 52 and thus to the patient outlet 54 is stopped. At this juncture, the force exerted on the piston 64 due to gas pressure in the chamber 50 is removed. This allows the stabilising spring 66 to relax and further push the piston 64 through to occlude further the gas inlet. Gas pressure behind the piston 58 falls as gas bleeds back through the line 74 and through the throttle unit towards the patient outlet 54, whereby the piston is restored to its original position under the action of the restoring spring 60, taking with it the valve element 64. The main gas inlet 46 is thus again able to supply gas to the throttle unit 52, and in this way the cyclic delivery of gas is continued.

Movement of the valve element 64 is restricted by an annular lip 76 on said element, which can come into engagement with O-ring seals 68 and 72 to limit the movement of the valve element in both directions.

In the automatic mode, the gas flow rate to the patient and the gas cycle periodicity are adjustable by means of the throttle unit 52.

For this purpose, the throttle unit 52 comprises a fixed sleeve 76 in which are longitudinally adjustable an outer hollow throttle neeedle 78 in screwthreaded engagement with the sleeve and an inner throttle needle 80 in screwthreaded engagement with the outer needle. The sleeve has a gas inlet 82 and gas outlets 84, 86, the first outlet 84 leading to the patient outlet 54 and the second outlet 86 to the line 74 through which a proportion of gas is supplied to the main valve 48.

The outer throttle needle 78 controls communication between the inlet 82 and the outlet 84, thereby to control the flow of gas to the patient. The inner throttle needle 80 controls communication between the inlet 82 and the outlet 86, thereby to determine the proportion of gas bled off to the main valve 48 to determine the gas cycle periodicity.

The inner needle is independently adjustable if desired, but adjustment of the outer needle to adjust patient gas flow also adjusts the gas cycle periodicity. This is the adjustment effected by the adult/child control 20 shown in FIG. 1.

Any discontinuity between the mating threads of the inner and outer throttle needles 80, 78 is taken up by the spring 88 acting on the flow-controlling head 90 of the inner needle 80.

FIG. 3 does not show the pressure relief valve 18 of FIG. 1, but this is provided at the patient outlet 54. However, FIG. 3 does show a respiratory relief valve 92 which becomes operative if the patient tries to inhale during a gas-off phase of the gas cycle. If the patient tries to inhale at this time, a negative pressure is created in branch line 94 leading to the valve 92, causing the valve element 96 to open. Immediately, therefore, prssure at the secondary inlet 56 of the main valve 48 is relieved, allowing the valve element 64 to open communication between the main valve inlet 46 and the outlet 50, whence a gas-on phase of the gas cycle is at once initiated.

Figure 4:
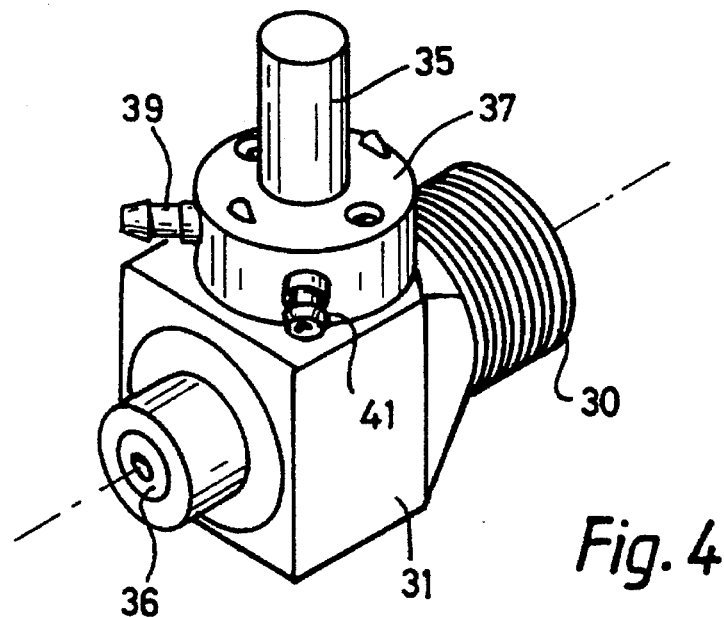
FIG. 4 shows the components of a part of the gas control circuit.

FIG. 4 illustrates how the regulator housing 31 is surmounted by a valve block 37. The housing 31 is provided with a cylindrical bore which receives a hollow valve spindle 35 extending upwardly through the block 37. The spindle 35 rotates within the housing 31 and the block 37 when the switch 16 is turned. The valve block 37 has two outlets 39, 41 which respectively lead gas to the line 38 or to the main inlet 46. The spindle 35 has a single radial port which connects a central hole in the spindle 35 either with the outlet 39 or the outlet 41, depending on the position of the switch 16. Hence, rotation of the switch 16 operates the valve (constituted by the valve spindle 35 and the valve block 37) to direct gas either to the manual valve 40 or the main valve 48.

Figure 5:
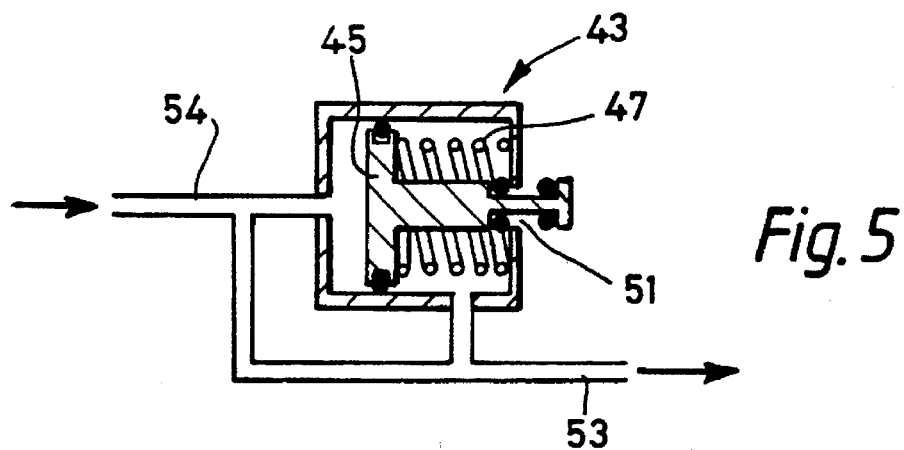
FIG. 5 shows an optional shuttle valve which can be incorporated in the patient outlet of the gas control circuit.
Figure 6:
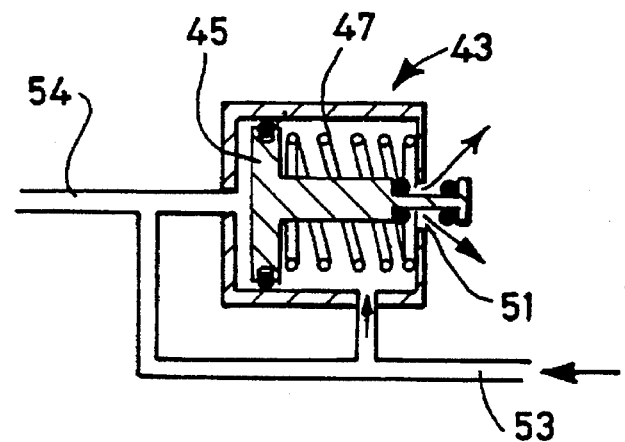
FIG. 6 shows the valve of FIG. 5 in another operative condition.

FIGS. 5 and 6 illustrate a shuttle valve 43 which can be incorporated in the line 54, just downstream of the branch line 94. The valve 43 has a piston 45 backed by a spring 47 which urges the piston 45 towards the left as viewed in FIGS. 5 and 6. Gas pressure in line 54 urges the piston 45 towards the right as viewed in FIGS. 5 and 6. When the piston 45 occupies either of its extreme positions, a seating 51 is closed. One such extreme position is shown in FIG. 5, when gas pressure in line 54 urges the piston 45 to the right and gas is supplied to the patient through line 53.

FIG. 6 illustrates how the valve 43 releases residual gas pressure in the lines 53 and 54 when gas is not supplied to the patient. In FIG. 6, the piston occupies an intermediate position and gas pressure in the lines 53 and 54 is relieved through the open seating 51.

We claim:

1. Breathing apparatus for supplying breathing gas to a patient, comprising a single housing adapted to be hand held, a gas inlet on the housing for connection to an inlet pipe to receive a continuous gas supply, a gas outlet on the housing, a face mask attached to the outlet, a gas circuit within the housing, a manually operable valve in the housing, the gas circuit including a main valve operative to produce a gas cycling effect, a switch on the housing whereby gas from the inlet is either supplied to the main valve and thereby automatically supplied by the gas circuit to the gas outlet on a cyclic basis or is supplied continuously to the manually operable valve in the housing, and a manually operable member on the housing for controlling the supply of gas to the outlet through the manually operable valve, in use with the face mask attached in the gas outlet the apparatus and the face mask form a contact combination the sole connection to which is provided by the inlet pipe, so that all adjustments and operations of the apparatus can be carried out by a user's fingers without the user needing to relax his hands holding the face mask in position.

2. Breathing apparatus according to claim 1, wherein the manually operable member is a trigger.

3. Breathing apparatus according to claim 1, wherein the gas circuit comprises a first adjustable throttle and a second adjustable throttle, wherein a flow rate of the gas to the patient is controlled by the first adjustable throttle and periodicity of a cycle of the cycling effect is controlled by the second adjustable throttle, the two throttles being respectively constituted by an inner throttle element and an outer throttle element arranged in a coaxial assembly, the inner throttle element being carried by the outer throttle element.

* * * * *